(12) United States Patent
Chikkala et al.

(10) Patent No.: US 11,764,981 B2
(45) Date of Patent: Sep. 19, 2023

(54) SECURELY TRANSMITTING DATA DURING AN AUDIO CALL

(71) Applicant: Merative US L.P., Ann Arbor, MI (US)

(72) Inventors: Ravithej Chikkala, Pflugerville, TX (US); Hamid Majdabadi, Ottawa (CA); Su Liu, Austin, TX (US); Manjunath Ravi, Austin, TX (US)

(*) Notice: Subject to any disclaimer, the term of this patent is extended or adjusted under 35 U.S.C. 154(b) by 378 days.

(21) Appl. No.: 16/817,970

(22) Filed: Mar. 13, 2020

(65) Prior Publication Data
US 2021/0288825 A1 Sep. 16, 2021

(51) Int. Cl.
| | |
|---|---|
| H04L 9/34 | (2006.01) |
| G16H 10/60 | (2018.01) |
| G16H 40/67 | (2018.01) |
| G16H 80/00 | (2018.01) |
| G06F 16/23 | (2019.01) |
| G06F 21/62 | (2013.01) |
| H04M 3/51 | (2006.01) |
| H04M 11/06 | (2006.01) |
| H04L 9/32 | (2006.01) |

(52) U.S. Cl.
CPC ............ *H04L 9/34* (2013.01); *G06F 16/2379* (2019.01); *G06F 21/6227* (2013.01); *G16H 10/60* (2018.01); *G16H 40/67* (2018.01); *G16H 80/00* (2018.01); *H04L 9/3247* (2013.01); *H04M 3/5158* (2013.01); *H04M 3/5166* (2013.01); *H04M 3/5183* (2013.01); *H04M 11/062* (2013.01); *H04M 2203/6009* (2013.01)

(58) Field of Classification Search
CPC ........ G16H 40/67; G16H 10/60; G16H 80/00; G06F 16/2379; G06F 21/6227; H04L 9/3247; H04M 3/5158; H04M 3/5166; H04M 3/5183; H04M 11/062
USPC .......................................... 713/176
See application file for complete search history.

(56) References Cited

U.S. PATENT DOCUMENTS

| | | | |
|---|---|---|---|
| 5,474,090 A | 12/1995 | Begun | |
| 5,704,364 A | 1/1998 | Saltzstein | |
| 6,219,408 B1 | 4/2001 | Kurth | |
| 8,301,232 B2 | 10/2012 | Albert | |
| 11,250,142 B1* | 2/2022 | Wu | H04L 9/0819 |
| 2007/0033072 A1 | 2/2007 | Bildirici | |
| 2011/0178799 A1 | 7/2011 | Allen | |
| 2013/0171930 A1* | 7/2013 | Anand | G07C 9/00182 |
| | | | 705/14.27 |
| 2019/0209022 A1* | 7/2019 | Sobol | A61B 5/0022 |
| 2021/0110060 A1* | 4/2021 | Sacks | G06F 21/602 |

OTHER PUBLICATIONS

Grady, Denise, "In Reporting Symptoms, Don't Patients Know Best?". The New York Times. Apr. 12, 2010, 5 pages, <https://www.nytimes.com/2010/04/13/health/13seco.html>.

(Continued)

*Primary Examiner* — Maria El-Zoobi
(74) *Attorney, Agent, or Firm* — Stephen J. Walder, Jr.

(57) ABSTRACT

Sharing data by defining a data encoding table, maintaining a data record database, defining a data encryption code, providing the data encryption code with an outgoing call, receiving an audio response including encrypted data, decrypting the encrypted data, and updating the data record database according to the data.

20 Claims, 5 Drawing Sheets

(56) References Cited

OTHER PUBLICATIONS

Mell et al., "The NIST Definition of Cloud Computing", Recommendations of the National Institute of Standards and Technology, NIST Special Publication 800-145, Sep. 2011, 7 pages.
Shaikh, Faizan, "Getting Started with Audio Data Analysis using Deep Learning (with case study)", Aug. 24, 2017, 34 pages, <https://www.analyticsvidhya.com/blog/2017/08/audio-voice-processing-deep-learning/>.

* cited by examiner

US 11,764,981 B2

SECURELY TRANSMITTING DATA DURING AN AUDIO CALL

BACKGROUND

The disclosure relates generally to securing data. The disclosure relates particularly to encrypting and securely sharing data during audio calls, such as telephone calls.

The Internet of Things environment produces large volumes of data relating to many aspects of user's lives, including health status, home and vehicle security, etc. Analysis and processing of this data requires providing the data to computing environments with sufficient resources which are programmed to receive and process the big data sets involved. Direct network connections having large bandwidths are not always available to transfer data from collecting devices to networked analysis environments.

Remote patient monitoring/telehealth diagnostics, including receiving actionable insights from patients at home leading to accurate treatment, can help to ease pressure on current healthcare systems, save lives and improve healthcare. Telehealth significantly affects long-term and post-acute care which reduces the need for admittance, thus reducing the associated care cost.

Hospitals/doctors may call patients periodically after the completion of a hospital stay. Patient care providers may have a "Patient Care Calling Program" to prepare patients and families for discharge from the hospital, improve patient and family satisfaction, and decrease hospital readmission rates. Patient Care Calling (e.g. post discharge follow-up phone call) is an essential part of supporting the patient from the time of discharge until his or her first appointment for follow-up care. Patients may be called 2 to 3 days after the hospital discharge/office visit by a member of the clinical staff.

This post-discharge follow-up phone call allows the patient's actions, questions, and misunderstandings, including discrepancies in the discharge plan, to be identified and addressed, as well as any concerns from caregivers or family members. Callers review each patient's: health status, medications, future appointments, scheduled home health services, and plans for what to do if a problem arises. Automated Patient Care Calling systems ask multiple questions and record patients answers.

Personal wearable devices (Oxygen Meter, Blood Pressure meter, Blood Sugar Meter, etc.) can monitor a user/patient conditions and output data using a network connection. Most households have access to basic telecommunications technology, like telephones, internet, and computers. Telehealth and telemedicine are a preferred method for post hospital care.

SUMMARY

The following presents a summary to provide a basic understanding of one or more embodiments of the disclosure. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatuses and/or computer program products enable the secure sharing of patient health monitoring data.

Aspects of the invention disclose methods, systems and computer readable media associated with the sharing of patient health data by defining a patient health data encoding table, maintaining a patient health record database, defining a patient data encryption code, providing the patient data encryption code during an outgoing patient care call, receiving a patient audio response including encrypted patient data, decrypting the encrypted patient data, and updating the patient health record database according to the received patient data.

Aspects of the invention disclose methods, systems and computer readable media associated with the sharing of patient health data by receiving patient health monitoring data from one or more connected health monitoring devices, creating a patient health care log according to the received data and a patient health data encoding table, detecting an incoming patient care call including an encryption code, encrypting the patient health care log according to an encryption code, and combining the encrypted patient health care log with outgoing patient audio response data.

Aspects of the invention disclose methods, systems and computer readable media associated with the sharing of patient health data by connecting to one or more patient health monitoring devices, receiving patient health monitoring data from the one or more connected health monitoring devices, creating a patient health care log according to the received data and a patient health data encoding table, detecting an incoming patient care call including an encryption code, encrypting the patient health care log according to the encryption code, and combining the encrypted patient health log with outgoing patient audio data.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Figure 1:
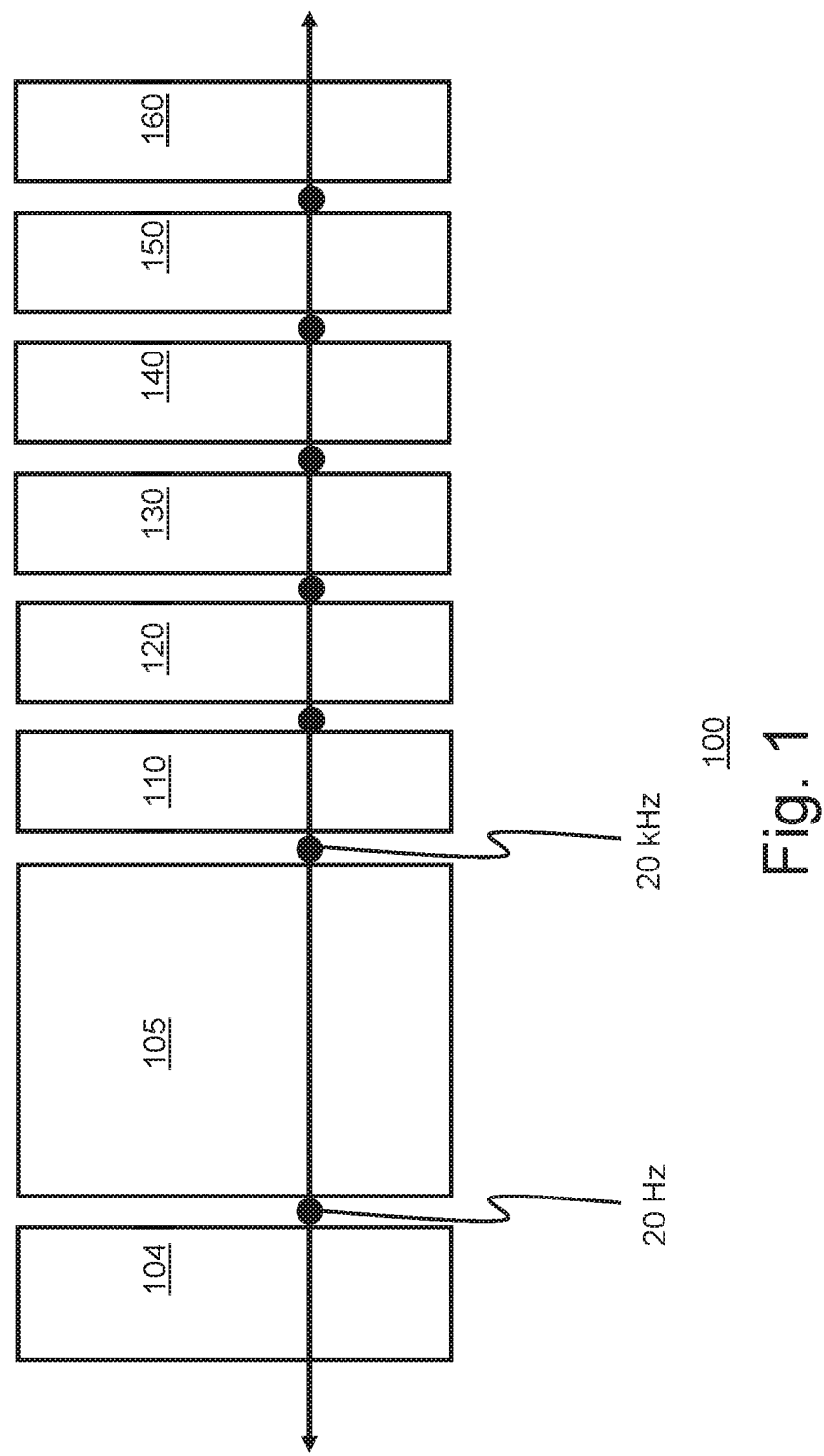
FIG. 1 illustrates a patient data encoding scheme, according to an embodiment of the invention.

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein.

In an embodiment, one or more components of the system can employ hardware and/or software to solve problems that are highly technical in nature (e.g., defining encoding tables, encrypting and decrypting data, etc.). These solutions are not abstract and cannot be performed as a set of mental acts by a human due to the processing capabilities needed to facilitate endpoint device remediation, for example. Further, some of the processes performed may be performed by a specialized computer for carrying out defined tasks related to memory operations. For example, a specialized computer can be employed to carry out tasks related to encrypting and decrypting patient data, logging and storing patient data or the like.

Though patient care calls to follow up on a patient's condition may reduce the need for follow up visits, not all patients can communicate all health-related insights and data. Patients may not be able to describe symptoms accurately during calls to medical centers when they are contacted for follow up.

Cognitively impaired individuals may not be capable of communicating pain or conditions verbally. Someone with Alzheimer's-type dementia loses short-term memory and cannot identify the source of recent painful areas and as a result, heath care professionals may not be able to help. Linguistic barriers in communication including accents, dialects and pidgin can also be a major contributor in misdiagnosis and missed diagnoses.

Continuous monitoring- or the remote observation of patient health related information at home—enables the collection of relevant patient health data but does not automatically convey this data to the care provider. Care providers require accurate communication, backed by supporting data, to reach a medial decision. Omissions may occur at each stage of the communications, where information is lost.

In some cases, personal wearable data cannot be easily and systemically uploaded to the remote medical diagnostics center and only covers the very basic range of a few symptoms. The data cannot replace specific prescribed medical monitoring devices for patients with specific need. Patient condition and activity may be monitored but requires manual configuration to extract and aggregate collected data.

Establishing a direct network connection between a patient device and a care provider's data server can be problematic. Not all patients possess access to the internet, and not all have digital communications equipment. Not all patients have the capacity to configure a direct network connection to a care providers system. Disclosed embodiments of the current invention provide methods and computer program products for the secure communication of patient monitoring data between remote patients and their care providers.

In an embodiment, patient health monitor data, logged from network connected patient health monitor devices, passes from the patient to a health care provider, or health care data storage system, during a patient care call. Through the disclosed methods, the logged data passes using a pre-configured client application, operating on a patient's computer or smartphone, communicating with a provider's server-side application operating in conjunction with the provider's call center equipment. During a patient care call, the server-side application establishes communication with the client-side application and the logged data held by the client-side application passes to the server-side application for analysis and storage.

The disclosed methods of the embodiments of the invention are carried out by software programs acting on a server-side and a client-side of a data sharing communication. In an embodiment, communication between the client and server applications occurs using a telephone connection, such as cellular phone connection between a smartphone running the client-side application and a server computing environment including telephone call center module. In an embodiment, the communications occur using a VOIP connection between the server environment and the client device. In an embodiment, the communications occur over an analog telephone system utilizing the microphone and speaker of a patient's device, such as a personal computer or tablet device.

The server environment may include a single, stand-alone server computer running the application, or a networked collection of computers running the application. In an embodiment, the server environment includes cloud, and/or edge cloud computing resources running the server-side application.

The client-side application operates upon a patient's smartphone, tablet, or computer, depending upon the nature of the device the patient chooses to use for the application and its associated communications with care providers.

In an embodiment, Encrypting Patient Condition Data (EPCD) server-side programs include an EPCD manager module which controls the overall EPCD process. The server-side EPCD program further includes an EPCD scheme repository holding at least one EPCD scheme which defines the patient data encoding table. In an embodiment, the encoding table specifies the format of communicated data including patient identification data, insurance information, applicable EPCD scheme, applicable EPCD repository, health condition data, patient appointment data, and patient personal health monitor data.

In an embodiment, as illustrated in FIG. 1, an EPCD scheme data encoding table (not pictured) associates ultrasonic portions of the audio spectrum 100 with various communicated data fields. FIG. 1 illustrates the parsing of the ultrasonic (>20 kHz) audio spectrum defining frequency ranges for each of health status 110, medications 120, appointments 130, home services 140, patient identifiers 150, and personal health monitor data 160. In an embodiment, the presence (1) and absence (0) of an ultrasonic carrier wave are used to communicate the binary encoded data associated with each portion of the spectrum. The audio portion of the spectrum 105, between 20 Hz and 20 kHz, remains undisturbed and is used for audio portions of the call. In this embodiment, the infrasonic portion 104, <20 hz, is not used. In an embodiment, any portion of the audio spectrum outside the 20 Hz-20 kHz range of human hearing, may be defined in the patient data table and then used for passing the patient data of the invention.

Table 1 provides an example of a patient data table, including data type and assigned ultrasonic frequency.

TABLE 1

| Data type | Frequency |
| --- | --- |
| Patient health status | 21 kHz |
| Medications | 21.5 kHz |
| Appointments | 22 kHz |
| Home health services | 22.5 kHz |
| Patient identification | 23 kHz |
| Monitor data | 23.5 kHz |

In an embodiment, all patient data may be parsed as to its order of presentation, configured as a comma separated variable (CSV) file and assigned to a single ultrasonic frequency for transmission.

In an embodiment, network connected health monitor devices include internet of things (IoT) smart watches, smart scales, or other devices connected to the patient's communications device, smartphone or voice over internet protocol (VOIP) device, by a wireless network connection such as WIFI, BLUETOOTH, BLUETOOTH LE, or similar wireless connections. In an embodiment, the patient configures the device used for the patient health data application, pairing the health care communication application device with each patient health monitor device to receive health data from the patient health monitor device(s). In this embodiment, patient health monitor devices monitor blood oxygen levels, blood pressure, heart rate, respiration rate, weight, and other patient health indicators. (Note: the term(s) "WIFI", "BLUETOOTH", and "BLUETOOTH LE" may be subject to trademark rights in various jurisdictions throughout the world and are used here only in reference to the products or services properly denominated by the marks to the extent that such trademark rights may exist.)

The client-side application receives the health monitor data from the patient health monitor devices and stores it in a client-side database between interactions with the server-side application. In an embodiment, the client-side database tracks the data according to the originating device and the time-stamp of the data, and passes this information to the server-side application with the logged data. In an embodiment, the client-side application clears the logged data after each interaction with the server-side application. In an embodiment, the client-side application archives the logged data in a client-side archive after sharing the data with the server-side application.

In an embodiment, establishing communications between the server-side and client-side application includes passing an EPCD encryption code, sending a digitally signed request for data, passing a pre-configured recognition code, or other similar actions, between the server-side and client-side applications. In response, the client-side application receives the encryption code, validates the digital signature, recognizes the pre-configured code or takes other steps as appropriate, to initiate the process of passing logged patient health monitor data.

The client-side application digitizes all data logged since the previous communication, including logged data and any changes to the patient's inventory of networked health monitoring devices. The client-side application encrypts the digitized data according to a pre-defined encryption algorithm and a shared encryption key. The client-side application then encodes the digitized data as an ultrasonic signal, or other predefined range of frequencies outside the range of human hearing. (The data is encoded according to a defined EPCD data table shared between the applications.) In an embodiment, the client-side application digitizes the ultrasonic signals and passes the digitized signals to the device for transmission with the digitized voice over IP data packets of the patient's responses during the patient care call. In an embodiment, superposed analog ultrasonic signals and analog voice signals are transmitted by the device.

In an embodiment, a patient using a landline uses a stand-alone device, such as a computer or tablet device, running the client-side application. In this embodiment, the microphone of the stand-alone device picks up the audio of the patient care call and extracts the ultrasonic portion of the signal using a high pass filter. The client-side application demodulates the ultrasonic signal yielding the encryption code and optional digital signature. The application validates the signature (when present) and proceeds as described above to the point of outputting the ultrasonic signal for transmission. In this embodiment, the speaker of the device outputs the ultrasonic signal during the call, the ultrasonic signal and encoded data, are then picked up by the microphone of the patient's telephone handset and relayed to the server-side application together with patient audio replies.

In an embodiment, the stand-alone device works in conjunction with an answering machine. In this embodiment, the client-side application of the stand-alone device scans incoming call audio for a trigger. (The trigger constitutes a pre-defined name or phrase selected as unlikely for any purpose other than triggering the actions of the client-side application.) After recognizing the trigger in incoming audio, the client-side application retrieves the logged data, parsed the data according to a data table, digitizes and encrypts the parsed data, encodes the encrypted binary string as ultrasonic and outputs the ultrasonic signal through the speaker of the stand-alone device.

Upon receipt, the server-side application extracts the ultrasonic data from the received audio file prior to any low-pass filtering by the receiving hardware. The server-side application demodulates the ultrasonic signal, yielding the encrypted binary string, decrypts the binary using the shared encryption key and parses the data according to the shared EPCD data table. The server-side application then updates the patient's database records with the new patient health monitor data.

In an embodiment, encoding the patient data as an ultrasonic signal enables the data to be appended to the digitized audio of the patient care call. The encoded data is added to the voice responses of the patient during the call. Encrypting the data protects the patient's privacy as the data passes to the server-side application. The ongoing receipt and storage of patient health monitor data enables care providers to observe trends in patient health dimensions. Data encryption and monitoring access to patient health data provides security for patient data.

In an embodiment, encrypting binary coded patient data occurs using an encryption algorithm of the method. In this embodiment, encryption algorithms include simple shared key encryption, as well as more complex encryption methods including the use of public-private key pairs and an encryption key created using Diffie-Hellman key pairs, using combinations of patient private key and provider public key, as well as provider private key and patient public key to create a shared encryption key which each party uses to encrypt and decrypt data. In an embodiment, an encryption key code passes from the server-side application to the client-side application as part of the patient care call. In this embodiment, the encryption—decryption algorithms are shared between the server-side and client-side portions of the overall application programs.

In an embodiment, the server-side application program maintains a database of patient health data. The database stores patient identification information as well as logged patient health monitor data collected using the communications method described herein. In an embodiment, the database includes a distributed database utilizing cloud or edge cloud resources as well as a HADOOP Distributed File system (HDFS) or similar file structure. The database includes patient profile information, including patient identification information, insurance information, and provider information, as well as patient status, health data, medication information, health care appointment information, home health services, and health monitoring device information. (Note: the term(s) "HADOOP" may be subject to trademark rights in various jurisdictions throughout the world and are used here only in reference to the products or services properly denominated by the marks to the extent that such trademark rights may exist.)

In an embodiment, the database includes a ledger. In this embodiment, the ledger includes ledger entries for each patient. The ledger entry includes a patient profile with identification information and a patient public key, patient health monitor data, and a record of all efforts to access the patient data. In an embodiment, each patient and provider using the disclosed methods, possesses a public-private key pair. In this embodiment, each communication requesting logged patient data is signed using a provider private key. Validation of the private key by using the requestor's public key enables access. An update to the patient's ledger entry records the access to data. New logged patient data, provided according to embodiments of the invention, carries a digital signature created using the patient's private key. Validation of this digital signature using the patient's public key enables an update of the patient's ledger entry to add the new data. In an embodiment, each patient profile includes a listing specifying the parties granted access to the patient's data and providing the public keys of those parties. Updates to the listing follow changes to the list of authorized parties.

Figure 2:
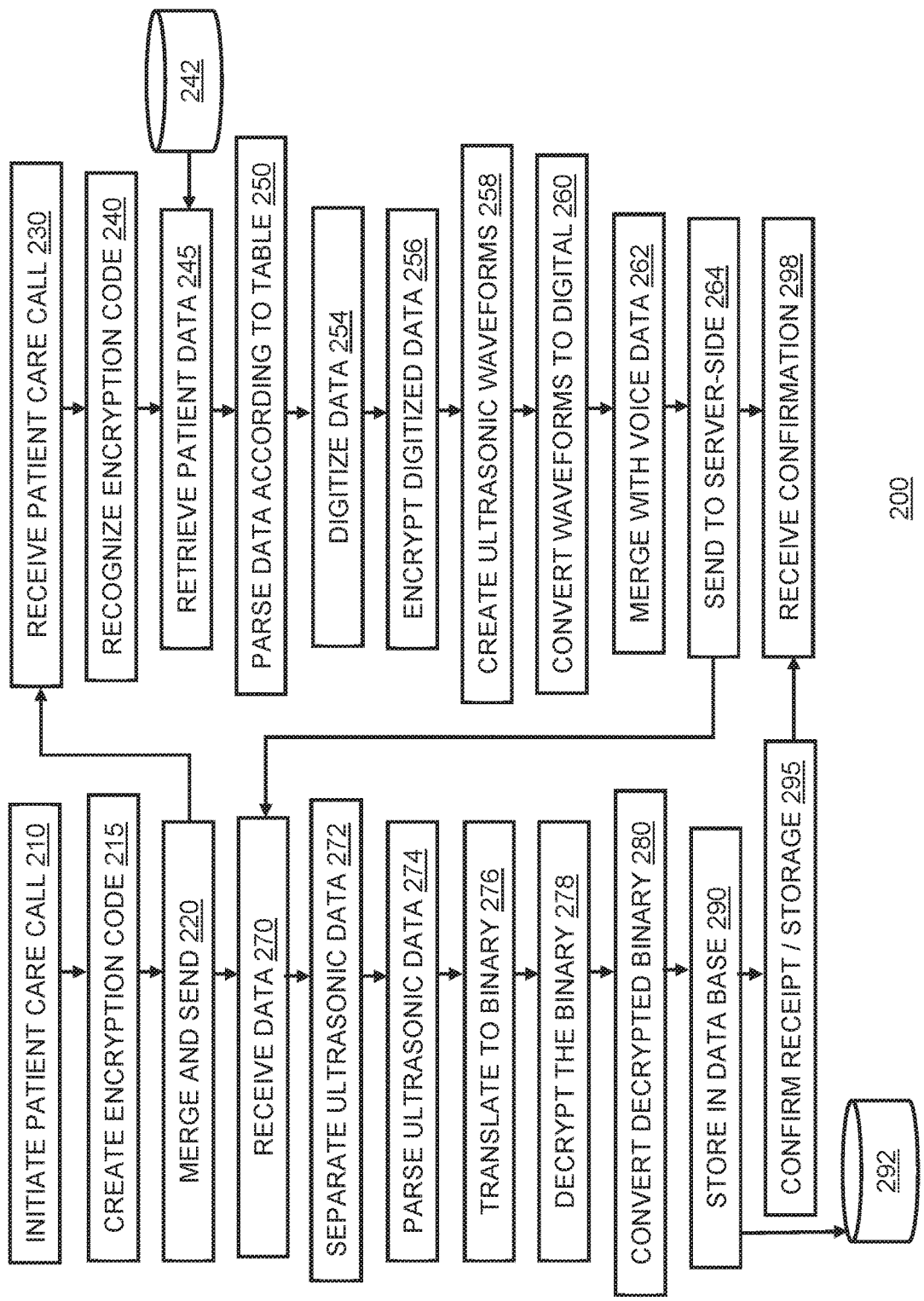
FIG. 2 provides flowcharts of server-side and client-side operational steps according to an embodiment of the invention.

In an embodiment, illustrated in flowchart 200 of FIG. 2, at block 210, a server-side patient call center module of EPCD program 375 of FIG. 3, described below, initiates a follow-up patient call. Patient care calls may be placed on a periodic basis, or triggered according to recent care events—office, urgent care, or hospital visits, medication refills, or other similar care events. At block 215, as part of the patient care call, the server-side application of EPCD program 375 creates a recognition or handshake signal, encodes the signal as ultrasonic data according to the EPCD data table and appends the signal to the outgoing audio of the patient care call at block 220. In an embodiment, the handshake signal includes an encryption code used to encrypt/decrypt data shared during the call. The handshake signal may be sent "as is" or may be encrypted according to a shared encryption algorithm. In response, at block 230, the client-side application of EPCD program 375, resident upon client devices 304 and 310 of FIG. 3 described below, receives the patient care call, separates the ultrasonic portion of the received call and recognizes the handshake signal—after decryption if needed, at block 240. The client-side application of EPCD program 375 retrieves logged patient monitor data, and any patient profile updates from a client side database 242, at block 245, at block 250, the client-side application of EPCD program parses the data according to the shared EPCD data table, digitizes the parsed data at block 254, encrypts the digitized parsed data using the shared encryption algorithm at block 256, creates virtual analog ultrasonic waveforms from the encrypted data according to the EPCD data table at block 258, virtually converts the ultrasonic waveforms from analog to digital data at block 260, and appends the digitized version of the ultrasonic waveform associated with the encrypted data to the outgoing patient voice data at block 262. The combined voice and ultrasonic data are sent to the server-side application of EPCD program 375 at block 264. In an embodiment, the encrypted data includes a digital signature composed using a private key of the patient. In an embodiment, encryption of the data occurs after the merger of the voice and ultrasonic data thereby passing only encrypted data to the server-side application at block 264.

The server-side application of EPCD program 375 receives the combination of ultrasonic and patient voice data at block 270, extracts the ultrasonic portion of the received data at block 272, parses the ultrasonic data according to the EPCD data table at block 274, and translates each parsed ultrasonic portion into a binary string at block 276. The server-side application of EPCD program 375 decrypts each binary string using the shared encryption algorithm at block 278 and converts the decrypted binary strings to ASCII or other character formats as appropriate at block 280. The conversion yields the original patient data sent by the client-side application. The server-side application then updates the patient's health records in the database 292, adding the new data at block 290. After updating the EPCD database with new data, the server-side application of EPCD program 375 sends a data receipt confirmation message to the client-side application at block 295, encoding the confirmation as ultrasonic data as described above. At block 298, the client-side application of EPCD program 375 receives the confirmation as described above and deletes, or archives, the logged data. In an embodiment, the client-side application of EPCD program 375 retains all logged data until the application has received the server-side data receipt confirmation message. In this embodiment, an interruption to the patient care call resulting in a partial or otherwise failed transfer of data results in ongoing data storage by the client-side application rather than the loss of data. In an embodiment, the digital signature of the patient is validated using the public key from the patient's database profile prior to adding the new data to the patient record.

In an embodiment (not shown) the server-side application begins the process by decrypting the entire received data string yielding the decrypted combination of voice and ultrasonic data. The decrypted data is then separated into voice and ultrasonic portions. The server-side application parses the ultrasonic data according to the EPCD data table and updates the patient's records in the database. In an embodiment (not shown), the server-side application extracts and decrypts the ultrasonic data, then parses the data according to the EPCD data table.

Figure 3:
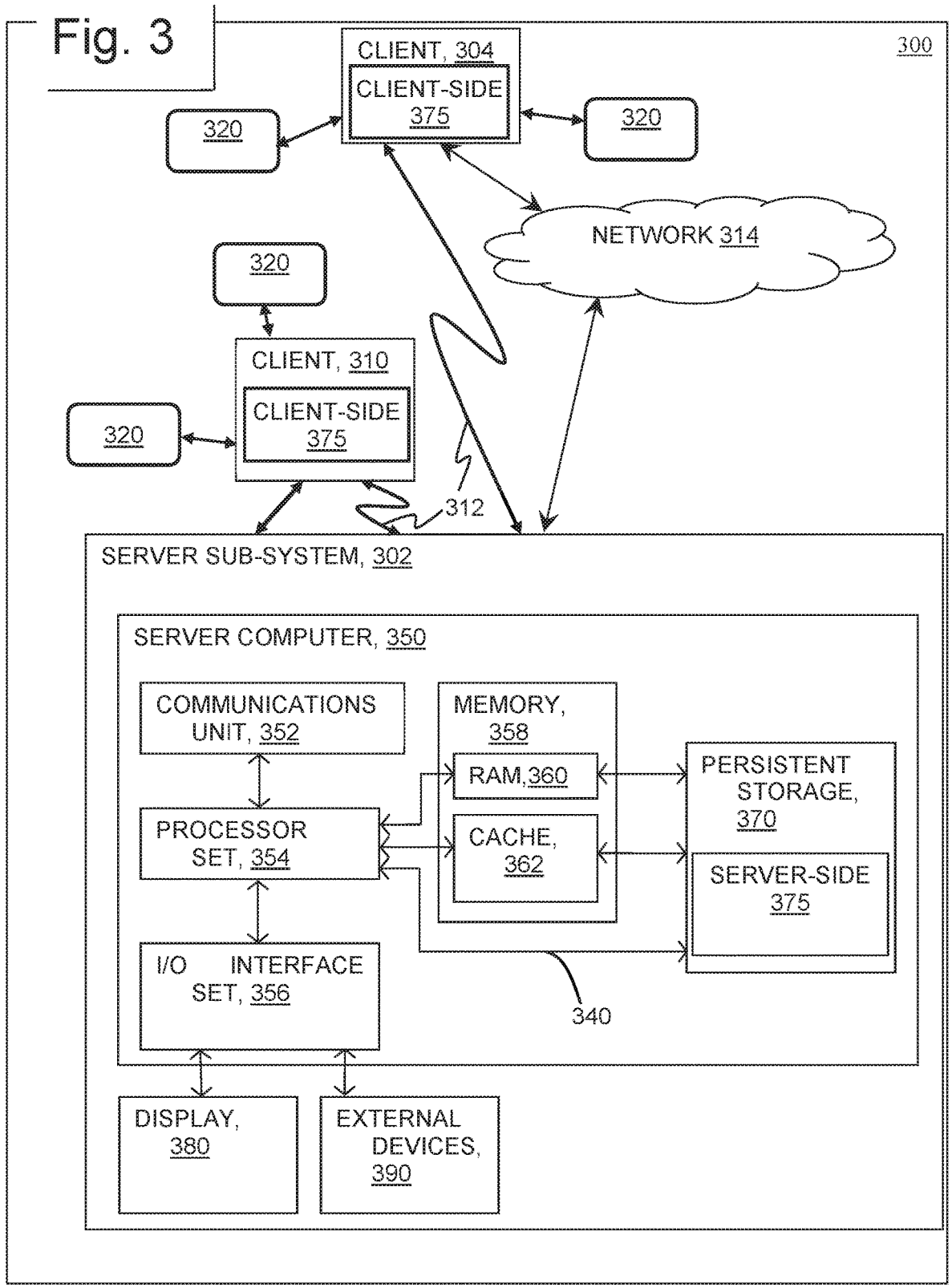
FIG. 3 provides a schematic illustration of exemplary network resources associated with practicing disclosed methods, according to an embodiment of the invention.

FIG. 3 provides a schematic illustration of exemplary network resources associated with practicing the disclosed inventions. The inventions may be practiced in the processors of any of the disclosed elements which process an instruction stream. As shown in the figure, a networked Client device 310 connects wirelessly to server sub-system 302. Client device 304 connects wirelessly to server sub-system 302 via network 314. Client devices 304 and 310 include the client-side application of EPCD program 375 together with sufficient computing resource (processor, memory, network communications hardware) to execute the program. Each of client devices 304 and 310 may further connect with server subsystem 302 by way of a wireless or wired telephone connection 312 for purposes of engaging with the server-side application of EPCD program 375 during a patient care call. As shown in FIG. 3, server sub-system 302 includes a server computer 350. FIG. 3 depicts a block diagram of components of server computer 350 within a networked computer system 300, in accordance with an embodiment of the present invention. It should be appreciated that FIG. 3 provides only an illustration of one implementation and does not imply any limitations with regard to the environments in which different embodiments can be implemented. Many modifications to the depicted environment can be made.

Server computer 350 can include processor(s) 354, memory 358, persistent storage 370, communications unit 352, input/output (I/O) interface(s) 356 and communications fabric 340. Communications fabric 340 provides communications between cache 362, memory 358, persistent storage 370, communications unit 352, and input/output (I/O) interface(s) 356. Communications fabric 340 can be implemented with any architecture designed for passing data and/or control information between processors (such as microprocessors, communications and network processors, etc.), system memory, peripheral devices, and any other hardware components within a system. For example, communications fabric 340 can be implemented with one or more buses.

Memory 358 and persistent storage 370 are computer readable storage media. In this embodiment, memory 358 includes random access memory (RAM) 360. In general, memory 358 can include any suitable volatile or non-volatile computer readable storage media. Cache 362 is a fast memory that enhances the performance of processor(s) 354 by holding recently accessed data, and data near recently accessed data, from memory 358.

Program instructions and data used to practice embodiments of the present invention, e.g., the EPCD program 375, are stored in persistent storage 370 for execution and/or access by one or more of the respective processor(s) 354 of server computer 350 via cache 362. In this embodiment, persistent storage 370 includes a magnetic hard disk drive. Alternatively, or in addition to a magnetic hard disk drive, persistent storage 370 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 370 may also be removable. For example, a removable hard drive may be used for persistent storage 370. Other examples include optical and magnetic disks, thumb drives, and smart cards that are inserted into a drive for transfer onto another computer readable storage medium that is also part of persistent storage 370.

Communications unit 352, in these examples, provides for communications with other data processing systems or devices, including resources of client computing devices 304, and 310. In these examples, communications unit 352 includes one or more network interface cards. Communications unit 352 may provide communications through the use of either or both physical and wireless communications links. Software distribution programs, and other programs and data used for implementation of the present invention, may be downloaded to persistent storage 370 of server computer 350 through communications unit 352.

I/O interface(s) 356 allows for input and output of data with other devices that may be connected to server computer 350. For example, I/O interface(s) 356 may provide a connection to external device(s) 390 such as a keyboard, a keypad, a touch screen, a microphone, a digital camera, and/or some other suitable input device. External device(s) 390 can also include portable computer readable storage media such as, for example, thumb drives, portable optical or magnetic disks, and memory cards. Software and data used to practice embodiments of the present invention, e.g., EPCD program 375 on server computer 350, can be stored on such portable computer readable storage media and can be loaded onto persistent storage 370 via I/O interface(s) 356. I/O interface(s) 356 also connect to a display 380.

Display 380 provides a mechanism to display data to a user and may be, for example, a computer monitor. Display 380 can also function as a touch screen, such as a display of a tablet computer.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
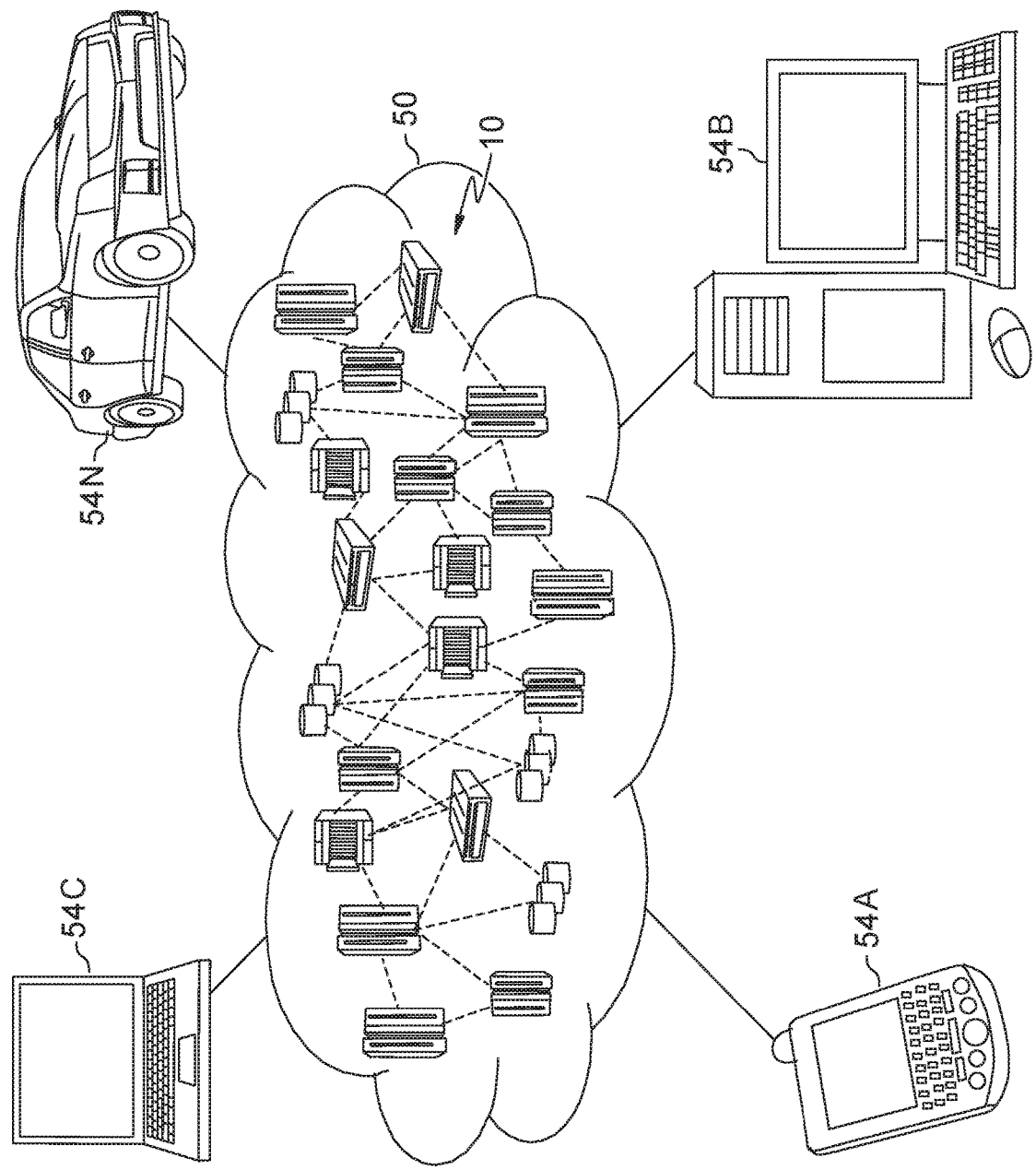
FIG. 4 depicts a cloud computing environment, according to an embodiment of the invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
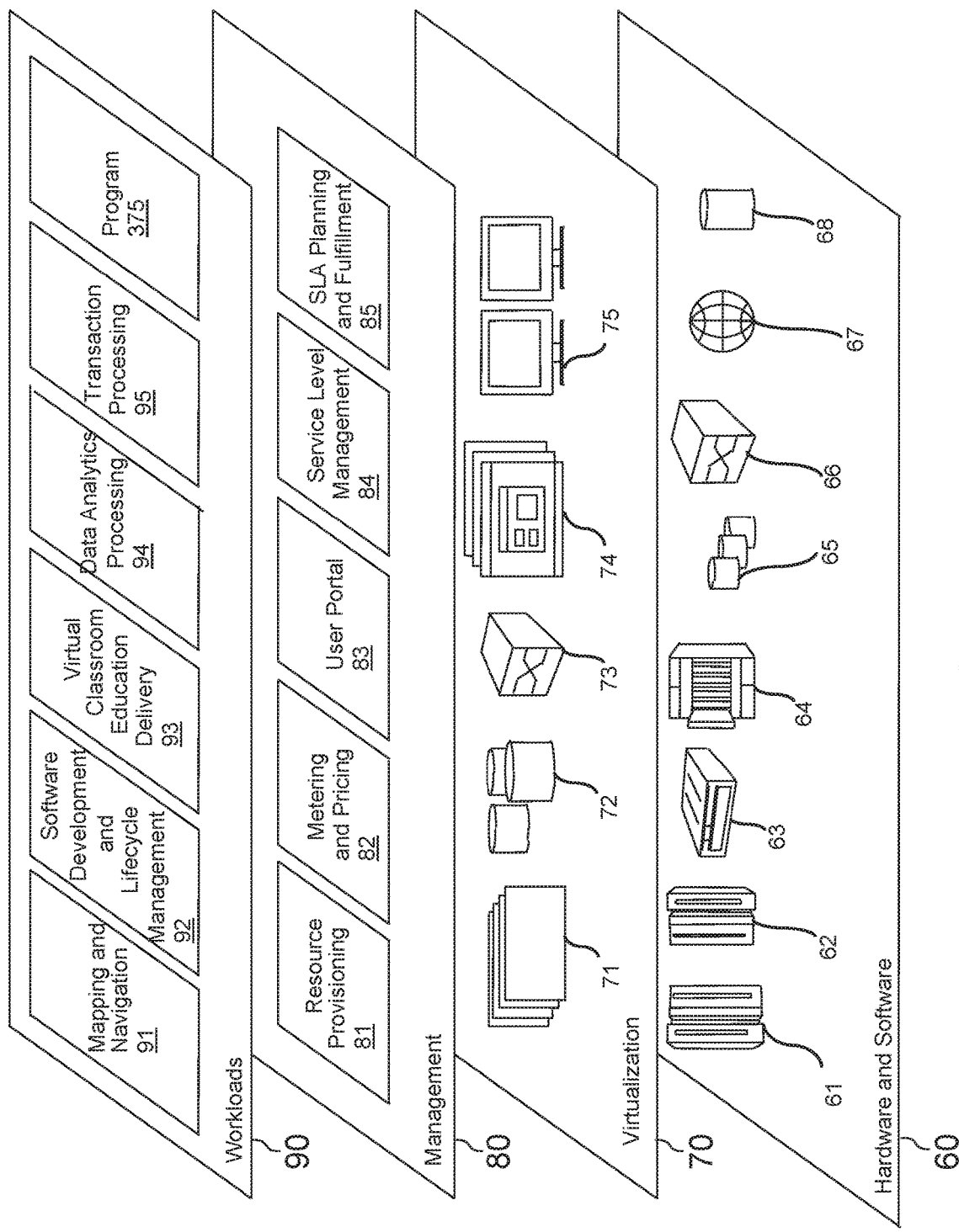
FIG. 5 depicts abstraction model layers, according to an embodiment of the invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and EPCD program 375.

The present invention may be a system, a method, and/or a computer program product at any possible technical detail level of integration. The invention may be beneficially practiced in any system, single or parallel, which processes an instruction stream. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein constitutes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer implemented method for sharing data, the method comprising:
  maintaining, by one or more computer processors, a data record database;

defining, by the one or more computer processors, a data encryption code;

providing, by the one or more computer processors, the data encryption code during an outgoing call;

receiving, by the one or more computer processors, during the call, an audio response including encrypted data;

decrypting, by the one or more computer processors, the data using the data encryption code; and updating, by the one or more computer processors, the data record database according to the data.

2. The computer implemented method according to claim 1, further comprising defining a data encoding table comprising data fields defined according to ultrasonic spectrum frequency ranges.

3. The computer implemented method according to claim 1, wherein maintaining the data record database comprises maintaining a record of patient health monitoring device data.

4. The computer implemented method according to claim 1, wherein the data encryption code comprises a digital signature.

5. The computer implemented method according to claim 1, wherein providing the data encryption code during an outgoing call comprises combining a digitized patient data encryption code with digitized outgoing audio data.

6. The computer implemented method according to claim 1, wherein providing the data encryption code with the outgoing call comprises combining an ultrasonic signal with an audible signal.

7. The computer implemented method according to claim 1, wherein updating the data record database comprises adding patient health monitoring device data to a patient health data record.

8. A computer program product for sharing patient health data, the computer program product comprising a non-transitory computer readable storage medium and program instructions collectively stored on the non-transitory computer readable storage medium, the program instructions comprising:
    program instructions to maintain a data record database;
    program instructions to define a data encryption code;
    program instructions to provide the data encryption code during an outgoing call;
    program instructions to receive an audio response including encrypted data;
program instructions to decrypt the data; and
    program instructions to update the data record database according to the data.

9. The computer program product according to claim 8, further comprising program instructions to define a data encoding table comprising data fields defined according to ultrasonic spectrum frequency ranges.

10. The computer program product according to claim 8, wherein maintaining the patient health record database comprises maintaining a record of patient health monitoring device data.

11. The computer program product according to claim 8, wherein the data encryption code comprises a digital signature.

12. The computer program product according to claim 8, wherein providing the data encryption code during an outgoing call comprises combining a digitized patient data encryption code with digitized outgoing audio data.

13. The computer program product according to claim 8, wherein providing the data encryption code with the outgoing call comprises combining an ultrasonic signal with an audible signal.

14. The computer program product according to claim 8, wherein updating the data record database comprises adding patient health monitoring device data to a patient health data record.

15. A computer system for sharing patient health data, the computer system comprising:
    one or more computer processors;
    one or more computer readable storage devices; and
    stored program instructions on the one or more computer readable storage devices for execution by the one or more computer processors, the stored program instructions comprising:
    program instructions to maintain a data record database;
        program instructions to define a data encryption code;
        program instructions to provide the data encryption code during an outgoing call; program instructions to receive an audio response including encrypted data;
program instructions to decrypt the data; and
    program instructions to update the data record database according to the data.

16. The computer system according to claim 15, further comprising program instructions to define a data encoding table comprising data fields defined according to ultrasonic spectrum frequency ranges.

17. The computer system according to claim 15, wherein maintaining the data record database comprises maintaining a record of patient health monitoring device data.

18. The computer system according to claim 15, wherein the data encryption code comprises a digital signature.

19. The computer system according to claim 15, wherein providing the data encryption code during an outgoing call comprises combining a digitized patient data encryption code with digitized outgoing audio data.

20. The computer system according to claim 15, wherein providing the data encryption code with the outgoing call comprises combining an ultrasonic signal with audible signal.

* * * * *